(12) United States Patent
Schenkel et al.

(10) Patent No.: US 8,648,321 B2
(45) Date of Patent: Feb. 11, 2014

(54) OPTICAL SENSOR FOR USE IN A DOMESTIC WASHING MACHINE OR DISHWASHER

(75) Inventors: Johann Schenkel, Pingarten (DE);
Martin Brabec, Nabburg (DE);
Manfredi Signorino, Milan (IT)

(73) Assignee: emz-Hanauer GmbH & Co. KGaA, Nabburg (DE)

( * ) Notice: Subject to any disclaimer, the term of this patent is extended or adjusted under 35 U.S.C. 154(b) by 334 days.

(21) Appl. No.: 12/830,375

(22) Filed: Jul. 5, 2010

(65) Prior Publication Data

US 2012/0001099 A1    Jan. 5, 2012

(51) Int. Cl.
*G01N 15/06* (2006.01)
*G01J 5/08* (2006.01)

(52) U.S. Cl.
USPC .................................... 250/573; 250/227.11

(58) Field of Classification Search
USPC ......... 250/227.11, 573–577, 216, 222.2, 239, 250/227.2, 227.24, 227.25, 227.31, 227.32; 356/436–442, 237.1, 239.1; 210/739, 210/745
See application file for complete search history.

(56) References Cited

U.S. PATENT DOCUMENTS

| | | | |
|---|---|---|---|
| 4,929,929 A | | 5/1990 | Romer |
| 4,935,621 A | * | 6/1990 | Pikulski ........................ 250/229 |
| 5,007,740 A | * | 4/1991 | Jeannotte et al. ............. 356/436 |
| 5,009,064 A | | 4/1991 | Grob et al. |
| 5,013,120 A | * | 5/1991 | Gergely et al. ................. 385/33 |
| 5,459,569 A | * | 10/1995 | Knollenberg et al. ........ 356/338 |
| 5,987,351 A | | 11/1999 | Chance |
| 2005/0101028 A1 | | 5/2005 | Kawamura et al. |
| 2009/0140754 A1 | * | 6/2009 | Schenkl et al. ............... 324/693 |
| 2010/0027015 A1 | | 2/2010 | Schweng et al. |

FOREIGN PATENT DOCUMENTS

| | | |
|---|---|---|
| DE | 2654726 B1 | 3/1978 |
| DE | 3839348 A1 | 6/1989 |
| DE | 3818416 C1 | 9/1989 |
| DE | 10133970 A1 | 2/2003 |
| DE | 10314923 A1 | 11/2004 |
| DE | 10344111 A1 | 5/2005 |
| DE | 102008050109 A1 | 1/2010 |
| EP | 0597566 A1 | 5/1994 |
| GB | 1598333 | 5/1981 |
| WO | 9116618 A1 | 10/1991 |
| WO | 2006050767 A2 | 5/2006 |

OTHER PUBLICATIONS

An English translation of an Office Action from the Chinese Intellectual Property Office dated Jan. 29, 2013, in a co-pending, counterpart application.

* cited by examiner

*Primary Examiner* — Pascal M Bui Pho
(74) *Attorney, Agent, or Firm* — Robert R. Deleault, Esq.; Mesmer & Deleault, PLLC

(57) ABSTRACT

An optical sensor for use in a washing machine or dishwasher comprises a housing, a light-emitting element, a light-receiving element and a light-conducting structure, which is made from a transparent material, having a light entry point, a first reflection surface, a second reflection surface and a light exit point. A light measurement path runs from the light-emitting element, via the light entry point, the first reflection surface, the second reflection surface and the light exit point, to the light-receiving element wherein the light undergoes total reflection on the first reflection surface and on the second reflection surface and where a light beam that runs from the first reflection surface to the second reflection surface has a cross-sectional area of not less than 0.9 mm$^2$.

15 Claims, 2 Drawing Sheets

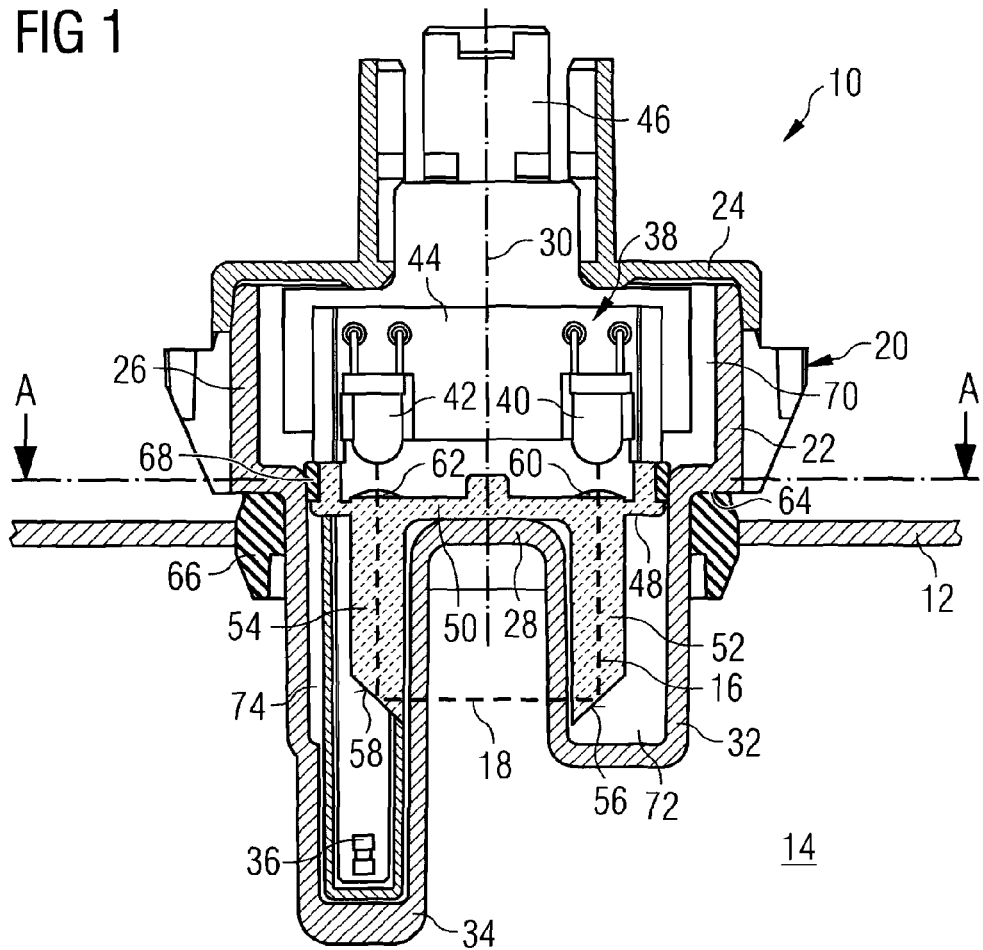
FIG 1
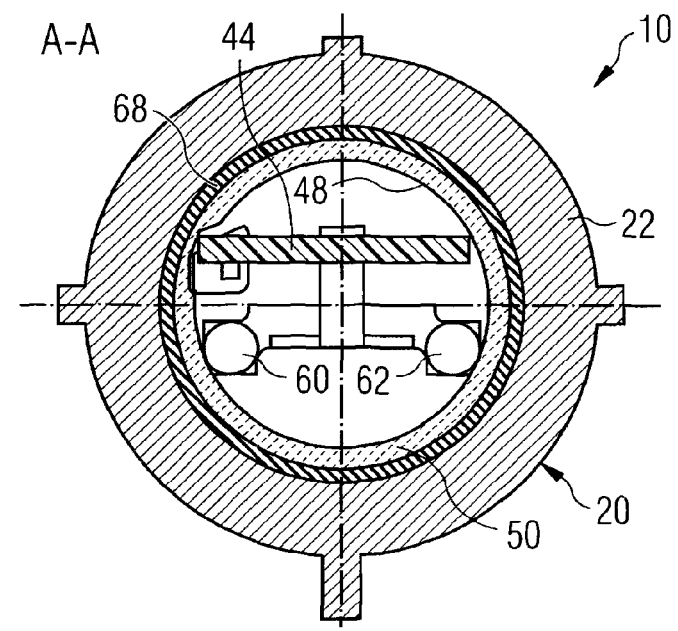
FIG 2  A-A

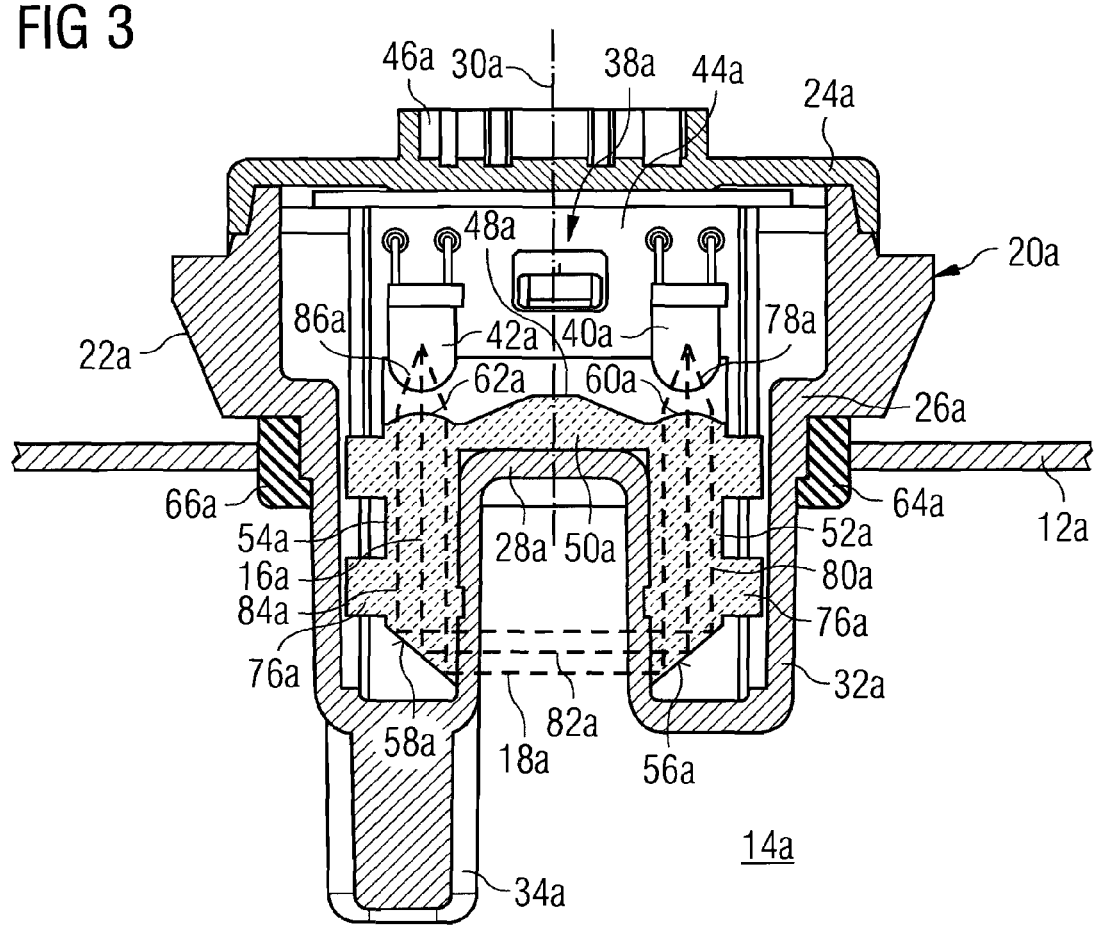

OPTICAL SENSOR FOR USE IN A DOMESTIC WASHING MACHINE OR DISHWASHER

The present disclosure relates to an optical sensor, intended for use in a domestic washing machine or dishwasher.

Optical sensors of the type considered here can be used, in particular, as turbidity sensors, by means of which the turbidity of the washing water can be determined in a washing machine or dishwasher. On the basis of the turbidity, conclusions can then be drawn concerning the degree of soiling of the laundry or dishes to be cleaned. To enable the turbidity of the washing water to be measured, a section of a light measurement path defined by the sensor runs, outside the sensor, through a washing chamber of the respective machine that is flushed by the washing water. On this section of the light measurement path running outside the sensor, light that is emitted along the light measurement path by the sensor undergoes attenuation that is dependent on the turbidity of the washing water.

Here, the term washing water represents any washing liquids used for cleaning the laundry or dishes. Generally, in addition to water, the washing liquid will also contain various additives, in particular cleaning substances, but also softeners or other accessory substances.

With regard to the prior art relating to optical sensors that can be used as turbidity sensors, reference is made, for example, to WO 2006/050767 A2.

An object is to provide an optical sensor that can be used as a turbidity sensor whose sensor output signal has a comparatively low susceptibility to faults.

According to one aspect, the invention provides an optical sensor for use in a washing machine or dishwasher, comprising a housing, a light-emitting element, a light-receiving element, and a light-conducting structure, made from a transparent material, having a light entry point, a first reflection surface, a second reflection surface and a light exit point. The light-emitting element, the light-receiving element and the light-conducting structure define a light measurement path that runs, in this sequence, from the light-emitting element, via the light entry point, the first reflection surface, the second reflection surface and the light exit point, to the light-receiving element. On a section located between the first and the second reflection surface, the light measurement path runs outside the housing, the light that reaches the light-receiving element, along the light measurement path, from the light-emitting element undergoing total reflection on the first reflection surface and on the second reflection surface. At each point on the section of the light measurement path that runs outside the housing, a light beam that runs from the first reflection surface to the second reflection surface has a cross-sectional area of not less than 0.9 mm$^2$.

In the case of domestic washing machines and dishwashers, numerous foreign particles (dirt particles), which separate from the material to be cleaned, can occur in the washing water. In addition, foaming is frequently observed in the washing water, which foaming can be caused or increased by, for example, cleaning additives. When such particles and foam bubbles cross the light measurement path, this can result in a temporary decrease in the sensor output signal, because the emitted light is scattered or absorbed by the particles and foam bubbles. When the particle or the foam bubble is rinsed back out of the light measurement path, the sensor output signal rises back to its previous value. The sensor output signal can decrease to a greater or lesser extent, depending on the size of the particles and foam bubbles. Such temporary decreases constitute a disturbing noise in the sensor output signal. It has been found that, with a certain minimum size of the light beam running from the first reflection surface to the second reflection surface, the disturbing influence of such particles and foam bubbles crossing the light measurement path can be reduced. Preferred values for the cross-sectional area of the light beam running from the first reflection surface to the second reflection surface are, in this sequence, 1.5 mm$^2$, 2.0 mm$^2$, 2.5 mm$^2$ and 3.0 mm$^2$.

Preferably, the light beam running from the first reflection surface to the second reflection surface is substantially a parallel beam.

Preferably, the entry point and/or the exit point has a collecting-lens function.

Preferably, a divergent light beam coming from the light-emitting element is converted by the collecting-lens function of the entry point into a substantially parallel light beam.

Preferably, a substantially parallel light beam coming from the second reflection surface is converted by the collecting-lens function of the exit point into a convergent light beam directed onto the light-receiving element.

Preferably, the first reflection surface and/or the second reflection surface is a planar surface.

Preferably, the light-conducting structure is constituted by an integrally coherent light-conducting body.

Preferably, the light-emitting element and/or the light-receiving element is/are arranged outside the light-conducting structure, at a distance from the latter.

According to a further aspect, the invention provides an optical sensor for use in a washing machine or dishwasher, comprising a housing, a light-emitting element, a light-receiving element, and a light-conducting structure, made from a transparent material, having a light entry point, a first reflection surface, a second reflection surface and a light exit point. The light-emitting element, the light-receiving element and the light-conducting structure define a light measurement path that runs, in this sequence, from the light-emitting element, via the light entry point, the first reflection surface, the second reflection surface and the light exit point, to the light-receiving element. On a section located between the first and the second reflection surface, the light measurement path runs outside the housing, the light that reaches the light-receiving element, along the light measurement path, from the light-emitting element undergoing total reflection on the first reflection surface and on the second reflection surface. The entry point and the exit point each have a collecting-lens function.

Preferably, a divergent light beam coming from the light-emitting element is converted by the collecting-lens function of the entry point into a substantially parallel light beam, this parallel light beam then being reflected on the first and the second reflection surface, and then being converted by the collecting-lens function of the exit point into a convergent light beam directed onto the light-receiving element.

Preferably, in the case of exclusively air being present on the section of the light measurement path that runs outside the housing, the radiant energy of the light arriving at the light-receiving element is at least 50 percent of the radiant energy of the light emitted from the light-emitting element in the direction of the entry point. Preferably, this proportion is at least 60 percent and, yet more preferably, at least 65 percent.

According to yet another aspect, the invention provides an optical sensor comprising a housing, which has a housing interior, and comprising a measuring assembly, which is arranged in the housing interior and which has a light-emitting element and a light-receiving element, the measuring assembly defining a light measurement path that runs from the light-emitting element to the light receiving element and that, on a portion of its path length, runs outside the housing.

The light-emitting element and the light-receiving element are arranged together in a first sub-chamber of the housing interior, and the light measurement path runs, on a portion of its path length, through at least one second sub-chamber of the housing interior that is sealed off in respect of the first sub-chamber. Preferably, all electrical/electronic components of the sensor are accommodated in the first sub-chamber, for instance evaluation electronics, arranged on a common printed circuit board, comprising the light-emitting element and the light-receiving element. It is thereby possible to ensure reliable protection against the penetration of washing water into those sensor regions where the electrical/electronic components of the sensor, including the light-emitting element and the light-receiving element, are located. Owing to the first sub-chamber being sealed off in respect of the at least one second sub-chamber, any ingress of washing water into the second sub-chamber does not result in a malfunction or even a failure of the electrical functioning of the sensor.

Expediently, the at least one second sub-chamber is constituted in a housing region that is intended for immersion in a chamber that is flushed by liquid. For best possible protection of the components of the measuring assembly that are accommodated in the first sub-chamber, the first sub-chamber is preferably delimited by such wall sections of the housing that are free from a liquid environment when the optical sensor is correctly mounted. This precludes washing water outside the housing from getting past the sealing point between the first and the second sub-chamber, through a perforation made unintentionally in the housing, for example during mounting or during use, and into the first sub-chamber.

In a preferred design, the measuring assembly comprises a light-conducting structure, made from a transparent material, which guides the light along a portion of the light measurement path. The light-conducting structure in this case has an entry point, open into the first sub-chamber, for a light beam coming from the light-emitting element and/or has an exit point, open into the first sub-chamber, for a light beam directed onto the light-receiving element. Further, it projects into the at least one second sub-chamber. The light-conducting structure preferably has two reflection surfaces that effect total reflection of the light guided along the light measurement path. In this case, a light beam directed from the light-emitting element onto the entry point of the at least one light-conducting body runs within the light-conducting structure as far as a first of the two reflection surfaces, where it undergoes total reflection in the direction of the second reflection surface, the portion of the light measurement path that is outside the housing being located between the two reflection surfaces. The light beam undergoes total reflection again on the second reflection surface and is then guided within the light-conducting structure as far as the exit point, from where it reaches the light-receiving element.

For the purpose of sealing off the first sub-chamber from the at least one second sub-chamber, the light-conducting structure can be sealed off in respect of the housing. For the purpose of sealing off the light-conducting structure in respect of the housing, a separate sealing element, for example, can be provided, inserted between the light-conducting structure and the housing. It is understood that, for example, a sealing element produced so as to be integral with the light-conducting structure can be provided instead of a separate sealing element. Conventional two-component injection techniques make it easy to produce a light-conducting structure having an integrally formed-on sealing element, which, if appropriate, is composed of a softer material than the light-conducting structure. Besides, it is also conceivable for the required sealing between the light-conducting structure and the housing to be realized in that the light-conducting structure is adhesive-bonded into the housing, the adhesive site providing the required tightness of seal. Moreover, it is conceivable for the required tightness of seal to be realized through a press fit of the light-conducting structure in the housing, or through a welded joint.

According to a preferred development, the housing has a cup-shaped housing main body, having a cup barrel and a cup bottom, which is realized with a plurality of protuberances, the light-conducting structure having a base part and having two elongations, which are integrally coherent with the base part and which project into each one of the protuberances. For the purpose of sealing off the first sub-chamber from the at least one second sub-chamber, the base part of the light-conducting structure can then be sealed off in respect of the cup barrel of the housing main body. For this purpose, it is recommended that the base part of the light-conducting structure fill the inner cross-section of the cup barrel substantially in its entirety. For example, the base part of the light-conducting structure can have a circular contour and sit in a correspondingly circular-cylindrical region of the cup barrel.

As an alternative to the light-conducting structure being mounted so as to be sealed off in respect of the housing, it is conceivable to provide a dividing membrane, which is separate from the light-conducting structure and transparent to the measuring light, and which extends transversely through the housing interior and divides the first sub-chamber in a sealing-off manner from the at least one second sub-chamber.

Although only a first and a second reflection surface have been mentioned hitherto in connection with the light-conducting structure, which can be produced, for example, in an injection moulding process, it is understood that the light-conducting structure can have in total more than two reflection surfaces for the purpose of deflecting the light provided by the light-emitting element and coupled into the light-conducting structure. It is easily conceivable for the light guided in the light-conducting structure to be deflected at three or more points by a reflection surface before it exits from the light-conducting structure at the exit point and reaches the light-receiving element. Thus, no limitation whatsoever is intended to the effect that the light-conducting structure should have only two reflection surfaces in total.

It is further pointed out that, instead of being realized through total reflection, the deflection of the light on the reflection surfaces can alternatively be realized, for example, through a mirrored realization of the reflection surfaces. Accordingly, no limitation whatsoever of the invention to total reflection of the light on the reflection surfaces is intended. It is sufficient if the reflection surfaces are designed in such a way that a deflection of the light beam guided in the light-conducting structure occurs on the reflection surfaces.

Preferred embodiments are explained in detail in the following with reference to the appended drawings, wherein:

FIG. 1 shows an axial longitudinal section through an optical sensor according to a first embodiment, FIG. 2 shows a sectional representation of the sensor of FIG. 1, according to the line A-A, FIG. 3 shows a schematic, axial longitudinal section through an optical sensor according to a second embodiment.

The optical sensor represented in FIGS. 1 and 2—which is denoted in general by the reference 10—is used as a turbidity sensor in a domestic washing machine or dishwasher. FIG. 1 shows the sensor 10 in the mounted state, the sensor being inserted in a mounting aperture (not denoted in greater detail) of a wall 12 delimiting a washing chamber 14 that is flushed by the washing water used to clean the laundry or the dishes. The sensor 10 emits light along a light measurement path, indicated by a broken line and denoted by the reference 16, a section 18 of which runs, outside the sensor, through the washing chamber 14. On this section, the light undergoes attenuation that is dependent on the degree of soiling (turbidity) of the washing water, the degree of soiling of the material (laundry, dishes) to be cleaned being deducible from the degree of attenuation.

The sensor 10 comprises a housing 20, which has an approximately cup-shaped housing main body 22 and has a cover part 24 placed upon the cup opening. The housing main body 22 has a cup barrel 26 and a cup bottom 28. The cup axis, denoted by the reference 30, of the cup-shaped housing main body 22 constitutes an axis of the housing 20. The cup bottom 28 has a plurality of axially projecting protuberances 32, 34 (here, two protuberances), which extend into the washing chamber 14 when the sensor 10 is in the mounted state. The protuberances 32, 34 can be of the same or differing configuration. In the example shown, the protuberance 34 has a greater axial length than the protuberance 32, this being due to the fact that a temperature sensor 36, which serves to sense the temperature of the washing water in the washing chamber 14, is accommodated in the protuberance 34.

Accommodated in the housing 20 of the sensor 10 is a measuring assembly, denoted in general by the reference 38, which comprises a light-emitting diode 40, serving as a light-emitting element, and comprises a photodiode 42, serving as a light-receiving element. It is understood that, instead of the light-emitting diode 40 and the photodiode 42, other types of light-emitting element and light-receiving element, respectively, can be used. The light-emitting diode 40 and the photodiode 42 are both arranged on a printed circuit board 44, on which, additionally, yet further electrical/electronic components can be accommodated. The printed circuit board 44 carries an electrical plug-in connector 46, via which the sensor 10 can be electrically connected to a control unit of the washing machine or dishwasher.

The measuring assembly 38 further comprises a light-conducting structure, which is made from a high-transparency material, for example polycarbonate and which, here, is constituted by a single light-conducting body 48. The light-conducting body 48 has a base part 50 and has two light-conducting fingers 52, 54 that protrude axially from the base part 50. Each of the light-conducting fingers 52 projects into one of the protuberances 32, 34 and, at least on a preponderant portion of its outer surface, is thereby surrounded by air, i.e. not in contact with the wall of the housing 20. At their free ends that project into the protuberance, the light-conducting fingers 52, 54 each have a reflection surface 56 and 58, respectively, here realized as a planar surface, which constitutes an optical interface from the material of the light-conducting body 48 to air and which causes the light running along the light measurement path 16 to undergo total reflection.

Integrally formed on the base part 50 of the light-conducting body 48 are two collecting lenses 60, 62, which are located approximately opposite the light-emitting diode 40 and the photodiode 42, and which constitute, respectively, a coupling-in point (entry point) for a light beam coming from the light-emitting diode 40 and a coupling-out point (exit point) for a light beam coming out of the light-conducting body 48. The collecting lens 60 in this case has such a characteristic that it renders approximately parallel the divergent light beam coming from the light-emitting diode 40, such that, in the light-conducting finger 52 of the light-conducting body 48, there runs a parallel light beam whose cross-sectional size corresponds approximately to that of the light-conducting finger 52. Accordingly, substantially the entirety of the reflection surface 56 provided at the free end of the light-conducting finger 52 is irradiated with light. The arriving parallel beam undergoes total reflection from the reflection surface 56 and emerges, through the housing wall of the protuberance 32, into the washing chamber 14. After passing along the path portion 18, this parallel beam goes through the housing wall of the protuberance 34 and enters the light-conducting finger 54. There, it undergoes total reflection on the reflection surface 58 and is conducted along the light-conducting finger 54, in the direction of the collecting lens 62. The collecting lens 62 converts the parallel beam into a convergent light beam, which is directed onto the photodiode 42.

In its axial region close to the bottom, the cup barrel 26 of the housing main body 22 has a radially inwardly stepped axial shoulder 64, which extends around in the manner of a ring and which serves as a seat for an outer sealing element 66 that seals off the sensor housing 20 in respect of the mounting wall 12. The outer sealing element 66 can be a separate sealing element, for example, or it can be realized, for instance in a two-component injection process, so as to be integrally coherent with the housing main body 22. The outer sealing element 66 prevents washing water from the washing chamber 14 from going through, between the housing and the mounting wall 12, into the (dry) chamber beyond the mounting wall 12.

On the inside of the sensor, the base part 50 of the light-conducting body 48 fills the inner cross-section of the housing main body 22 substantially in its entirety, being sealed off in respect of the housing main body 22 by an inner sealing element 68 that extends around in the manner of a ring. This inner sealing element 68 can be produced separately from the light-conducting body 48 and the housing main body 22, and inserted between these two components. Alternatively, it is conceivable for the inner sealing element 68 to be produced such that it is integrally coherent with the light-conducting body 48. Within the housing 20 of the sensor 10, the base part 50 of the light-conducting body 48 divides a first sub-chamber 70, in which the light-emitting diode 40, the photodiode 42 and any other electrical/electronic components of the measuring assembly 38 are located, from two sub-chambers 72, 74, which are constituted at least in the protuberances 32, 34 and which each accommodate one of the light-conducting fingers 52, 54. The first sub-chamber 70 in this case is sealed off in respect of each of these two sub-chambers 72, 74 by the inner sealing element 68. Therefore, in the event of any ingress of washing water into one of the two sub-chambers 72, 74, the inner sealing element 68 prevents the entered washing water from passing through into the first sub-chamber 70.

In the case of an alternative design, it is conceivable for the light-conducting fingers 52, 54 to be realized, not in an integrally coherent manner on a common light-conducting body, but to be separately produced components, each of these components being sealed off, in respect of the wall of one of the protuberances 32, 34, by a respective inner sealing element.

It can be seen in FIG. 1 that, in respect of the outer sealing element 66, the inner sealing element 68 is offset axially somewhat away from the washing chamber 14. The result of this is that ingress of water from the washing chamber 14, through one of the second sub-chambers 72, 74, into the first sub-chamber 70 is always obstructed by the inner sealing element 68, and that direct ingress of washing water from the washing chamber 14 into the first sub-chamber 70 is not possible.

In other words, this relative axial position of the inner sealing element 68 in relation to the outer sealing element 66 results in the first sub-chamber 70 being delimited solely by such wall parts of the housing 20 that, in the mounted state shown in FIG. 1, have no contact with the washing water in the washing chamber 14, i.e. are free from a liquid environment.

It is understood that the housing main body 22 is realized to be sufficiently transparent, at least in those regions in which the light running along the light measurement path 16 passes through its wall, a certain cloudiness of the material of the housing main body 22 being easily possible.

It is further understood that a tight connection between the base part 50 of the light-conducting body 48 and the housing main body 22 can also be achieved through pressing, welding or adhesive bonding. An additional sealing body, for instance in the form of the inner sealing element 68, can be dispensed with in this case.

It has already been explained that the collecting lens 60 causes a light beam that is emitted from the light-emitting diode 40 in the direction of the collecting lens 60 to be rendered as parallel as possible. This parallelized light beam is then conducted in the light-conducting body 48, without significant divergence alteration, as far as the collecting lens 62, where it is directed onto the photodiode 42. The cross-sectional form of the light beam guided in the light-conducting body 48 is, for example, circular, the light-conducting fingers 52, 54 of the light-conducting body 48 likewise having, for example, a circular cross-section. The diameter of the light beam guided in the light-conducting body 48 can be, for example, at least 1 mm or at least 1.5 mm or at least 2 mm. In the case of a possible design of the sensor 10, the diameter of this light beam can be, for example, approximately 2.4 mm. This results—assuming a circular beam cross-section—in a beam cross-sectional area of approximately 4.5 mm$^2$. Such a magnitude of the cross-sectional area of the light beam guided in the light-conducting body 48 is advantageous for ensuring that disturbances, which can be caused by any particles or foam bubbles that cross the section 18 of the light measurement path 16, are as few as possible. If such a particle, floating in the washing water, has a size of, for example, a few tenths of a millimetre, the particle causes only a comparatively small attenuation of the output signal delivered by the sensor 10. Complex time-averaging of the sensor output signal for the purpose of eliminating the effect of crossing particles or foam bubbles can perhaps thus be avoided.

The parallelization, by the collecting lens 60, of the light beam entering the light-conducting body 48 and the subsequent parallel guidance of this light beam in the light-conducting body 48 as far as the collecting lens 62 on the exit side ensure that a substantial portion of the radiant energy irradiated into the light-conducting body 48 from the light-emitting diode 40 arrives at the photodiode 42, and that the radiation losses along the light measurement path 16 are only comparatively small. For example, the radiant energy coupled out of the light-conducting body 48 and arriving at the photodiode 42 can be over 70% of the radiant energy of the light beam emitted from the light-emitting diode 40 in the direction of the collecting lens 60, assuming the presence of air on the portion 18 of the light measurement path 16.

It can also be seen in FIG. 1 that both the light-emitting diode 40 and the photodiode 42 are arranged at a distance from the light-conducting body 48, outside the latter, i.e. they do not project—as in WO 2006/050767 A2, see therein e.g. FIGS. 1 and 3—into pockets of the light-conducting body.

Reference is now made to FIG. 3. In the case of the second embodiment shown therein, components that are the same, or have the same function, as in the case of the first embodiment are denoted with the same references as in FIGS. 1, 2, but with a lower-case letter suffix. To avoid unnecessary repetitions, reference is made to the preceding explanations relating to such components that are the same or have the same function, unless stated otherwise in the following.

In the case of the sensor 10a according to the second embodiment, the interior of the housing 20a is not subdivided into sub-chambers that are sealed off from one another. The light-conducting body 48a has, on its light-conducting fingers 52a, 54a, a plurality of laterally projecting support ribs 76a, which serve to fix the light-conducting body 48a in mounting grooves of the housing 20a, which are not represented in greater detail.

Additionally in FIG. 3, the light beams running along the light measurement path 16a are indicated by broken lines. The figure shows a divergent light beam 78a that is directed from the light-emitting diode 40a in the direction of the collecting lens 60a and that is converted into a parallel beam 80a by the collecting lens 60a. This parallel beam 80a runs in the light-conducting finger 52a as far as the reflection surface 56a. There, the parallel beam 80a undergoes total reflection and runs, as a parallel light beam 82a, through the measurement gap (corresponding to the portion 18a of the light measurement path 16a) constituted between the protuberances 32a, 34a of the housing 20a, until it is incident upon the reflection surface 58a. There, it undergoes further total reflection. The light runs, as a parallel light beam 84a, from the reflection surface 58a in the direction of the collecting lens 62a, where it is converted into a convergent light beam 86a.

The refractive power of the collecting lens 60a can be substantially equal to the refractive power of the collecting lens 62a. It is of course understood that, alternatively, the collecting lenses 60a, 62a can have differing magnitudes of refractive power, for example depending, inter alia, on the directivity characteristics of the light-emitting diode 40a and of the photodiode 42a.

The invention claimed is:

1. A washing machine and/or dishwasher having a wall delimiting a space flushed with water, the washing machine and/or dishwasher comprising:
    an optical sensor which is mounted to the wall delimiting the space flushed with water of the washing machine and/or dishwasher, the optical sensor comprising:
        a housing;
        a light-emitting element;
        a light-receiving element; and
        a light-conducting structure, made from a transparent material, having a light entry point, a first reflection surface, a second reflection surface and a light exit point, a collecting-lens mechanism at the light entry point of the light-conducting structure coupling light from the light-emitting element into the light conducting structure where a divergent light beam coming from the light-emitting element is converted by the collecting-lens function of the entry point into a substantially parallel light beam;
    the light-emitting element, the light-receiving element and the light-conducting structure defining a light measurement path that runs, in this sequence, from the light-emitting element, via the light entry point, the first reflection surface, the second reflection surface and the light exit point, to the light-receiving element;
    on a section located between the first reflection surface and the second reflection surface, the light measurement path running outside the housing and in the space flushed with water;
    the light-emitting element, the collecting-lens mechanism at the light entry point of the light-conducting structure, and the first reflection surface producing a light beam that at each point on the section of the light measurement path that runs outside the housing from the first reflection surface to the second reflection surface having a cross-sectional area of not less than 0.9 mm$^2$ wherein the light beam arriving at the light-receiving element is at least 50% of the light beam from the light-emitting element and wherein the cross-sectional area of the light beam reduces a disturbing influence of particles and/or foam bubbles crossing the light measurement path.

2. The washing machine and/or dishwasher according to claim 1, the light beam having a cross-sectional area of not less than 1.5 mm$^2$.

3. The washing machine and/or dishwasher according to claim 1, the light beam having a cross-sectional area of not less than 2.0 mm$^2$.

4. The washing machine and/or dishwasher according to claim 1, the light beam having a cross-sectional area of not less than 2.5 mm$^2$.

5. The washing machine and/or dishwasher according to claim 1, the light beam having a cross-sectional area of not less than 3.0 mm$^2$.

6. The washing machine and/or dishwasher according to claim 1, the exit point having a collecting-lens function.

7. The washing machine and/or dishwasher according to claim 6, the substantially parallel light beam coming from the second reflection surface being converted by the collecting-lens function of the exit point into a convergent light beam directed onto the light-receiving element.

8. The washing machine and/or dishwasher according to claim 6, the substantially parallel light beam reflected on the first and the second reflection surfaces, and then converted by the collecting-lens function of the exit point into a convergent light beam directed onto the light-receiving element.

9. The washing machine and/or dishwasher according to claim 8, in the case of exclusively air being present on the section of the light measurement path that runs outside the housing, the radiant energy of the light arriving at the light-receiving element being at least 50 percent of the radiant energy of the light emitted from the light-emitting element in the direction of the entry point.

10. The washing machine and/or dishwasher according to claim 9, the radiant energy of the arriving light being at least 60percent of the radiant energy of the light emitted in the direction of the entry point.

11. The washing machine and/or dishwasher according to claim 9, the radiant energy of the arriving light being at least 65percent of the radiant energy of the light emitted in the direction of the entry point.

12. The washing machine and/or dishwasher according to claim 1, the first reflection surface and/or the second reflection surface being a planar surface.

13. The washing machine and/or dishwasher according to claim 1, the light-conducting structure being constituted by an integrally coherent light-conducting body.

14. The washing machine and/or dishwasher according to claim 1, the light-receiving element being arranged outside the light-conducting structure, at a distance from the latter.

15. The washing machine and/or dishwasher according to claim 1, wherein the collecting-lens mechanism at the light entry point of the light-conducting structure is integrally formed on a base of the light-conducting structure.

* * * * *